(12) United States Patent
Vermeiren

(10) Patent No.: US 10,798,502 B2
(45) Date of Patent: Oct. 6, 2020

(54) IMPLANTABLE TRANSDUCER SYSTEM

(71) Applicant: Cochlear Limited, Macquarie University, NSW (AU)

(72) Inventor: Jan Vermeiren, Mechelen (BE)

(73) Assignee: COCHLEAR LIMITED, Macquarie University NSW (AU)

( * ) Notice: Subject to any disclaimer, the term of this patent is extended or adjusted under 35 U.S.C. 154(b) by 576 days.

(21) Appl. No.: 15/299,703

(22) Filed: Oct. 21, 2016

(65) Prior Publication Data
US 2018/0115842 A1 Apr. 26, 2018

(51) Int. Cl.
*H04R 25/00* (2006.01)

(52) U.S. Cl.
CPC .... *H04R 25/606* (2013.01); *A61F 2220/0016* (2013.01); *A61F 2250/001* (2013.01); *H04R 2225/67* (2013.01)

(58) Field of Classification Search
CPC .... H04R 25/60; H04R 25/604; H04R 25/606; H04R 25/608; H04R 2225/67; H04R 2225/77; H04R 25/65; H04R 25/652; H04R 25/656
See application file for complete search history.

(56) References Cited

U.S. PATENT DOCUMENTS

| | | | |
|---|---|---|---|
| 6,293,903 B1 * | 9/2001 | Kasic, II | H04R 25/606 600/25 |
| 6,325,755 B1 * | 12/2001 | Bushek | H04R 25/606 600/25 |
| 6,712,754 B2 | 3/2004 | Miller et al. | |
| 6,807,445 B2 | 10/2004 | Baumann et al. | |
| 7,137,946 B2 | 11/2006 | Waldmann | |
| 7,214,179 B2 | 5/2007 | Miller, III et al. | |
| 7,618,450 B2 | 11/2009 | Zarowski et al. | |
| 8,192,488 B2 | 6/2012 | Lesinski et al. | |
| 8,380,288 B2 | 2/2013 | Labadie et al. | |
| 8,886,331 B2 | 11/2014 | Labadie et al. | |
| 9,167,362 B2 | 10/2015 | Koskowich | |
| 2003/0065245 A1 * | 4/2003 | Easter | H04R 25/606 600/25 |

(Continued)

FOREIGN PATENT DOCUMENTS

| CN | 101690266 A | 3/2010 |
|---|---|---|
| CN | 103037807 A | 4/2013 |

(Continued)

OTHER PUBLICATIONS

International Search Report and Written Opinion in corresponding International Application No. PCT/IB2017/056367, dated Feb. 13, 2018, 11 pgs.

*Primary Examiner* — Carrie R Dorna
(74) *Attorney, Agent, or Firm* — Edell, Shapiro & Finnan, LLC

(57) ABSTRACT

Embodiments are generally directed to implantable transducer systems for implantable hearing prostheses. The implantable transducer systems in accordance with embodiments presented herein include a transducer and an expandable fixation arrangement, such as a radially expandable fixation arrangement, that is configured to anchor/secure the implantable transducer system directly within an elongate cannular cavity extending through a portion of a recipient's skull bone.

24 Claims, 10 Drawing Sheets

(56) References Cited

U.S. PATENT DOCUMENTS

| | | | |
|---|---|---|---|
| 2004/0147804 A1* | 7/2004 | Schneider | H04R 25/606 600/25 |
| 2005/0101830 A1* | 5/2005 | Easter | H04R 25/606 600/25 |
| 2006/0034473 A1* | 2/2006 | Halteren | H04R 25/604 381/322 |
| 2008/0249351 A1 | 10/2008 | Schneider et al. | |
| 2009/0131742 A1* | 5/2009 | Cho | H04R 25/606 600/25 |
| 2012/0239113 A1 | 9/2012 | Vermeiren | |
| 2013/0006044 A1* | 1/2013 | Menzl | H04R 25/606 600/25 |
| 2013/0165737 A1 | 6/2013 | Van Den Heuvel | |
| 2013/0178855 A1 | 7/2013 | Loquet et al. | |
| 2014/0056453 A1* | 2/2014 | Olsen | H04R 25/02 381/328 |
| 2014/0270293 A1* | 9/2014 | Ruppersberg | H04R 25/606 381/318 |
| 2016/0059013 A1 | 3/2016 | Van Vlem | |

FOREIGN PATENT DOCUMENTS

| | | |
|---|---|---|
| CN | 103404175 A | 11/2013 |
| CN | 103718571 A | 4/2014 |
| CN | 105188608 A | 12/2015 |
| KR | 101548344 B1 | 9/2015 |
| WO | 2010/089420 A2 | 8/2010 |

\* cited by examiner

IMPLANTABLE TRANSDUCER SYSTEM

BACKGROUND

Field of the Invention

The present invention relates generally to implantable transducer systems for implantable hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals suffering from conductive hearing loss typically receive an acoustic hearing aid. Hearing aids rely on principles of air conduction to transmit acoustic signals to the cochlea. Typically, a hearing aid is positioned in the ear canal or on the outer ear to amplify received sound. This amplified sound is delivered to the cochlea through the normal middle ear mechanisms resulting in the increased perception of sound by the recipient.

In contrast to acoustic hearing aids, certain types of implantable auditory prostheses, sometimes referred to as implantable acoustic auditory prostheses, convert a received sound into output mechanical force (vibration) for delivery to the recipient. The vibrations are transferred through the recipient's, teeth, bone, and or other tissue to the cochlea. The vibrations cause movement of the cochlea fluid that generates nerve impulses resulting in perception of the received sound by the recipient. Acoustic auditory prostheses are suitable to treat a variety of types of hearing loss and may be prescribed for individuals who cannot derive sufficient benefit from acoustic hearing aids, cochlear implants, etc., or for individuals who suffer from stuttering problems. Implantable acoustic auditory prostheses include, for example, bone conduction devices, middle ear auditory prostheses (middle ear implants), direct acoustic stimulators (direct cochlear stimulators), or other partially or fully implantable auditory prosthesis that deliver vibrations to a recipient to directly or indirectly generate movement of the cochlea fluid.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are a type of implantable auditory prosthesis that are often proposed when the sensorineural hearing loss is due to the absence or destruction of the cochlea hair cells, which transduce acoustic signals into nerve impulses. An auditory brainstem stimulator is another type of implantable stimulating auditory prosthesis that might also be proposed when a recipient experiences sensorineural hearing loss due to damage to the auditory nerve.

SUMMARY

In one aspect of the invention, an implantable transducer system is provided. The implantable transducer system comprises: a transducer configured for insertion into a cannular cavity formed in a recipient; and a radially expandable fixation arrangement attached to the transducer and configured to anchor the transducer at a location within the cannular cavity.

In another aspect of the present invention, an implantable transducer system configured to be positioned in a cannular cavity formed in a recipient is provided. The implantable transducer system comprises: an implantable transducer; and a fixation arrangement coupled to the implantable transducer and comprising at least one expandable element having a first compressed configuration to facilitate insertion into the cannular cavity and a second expanded configuration that is activated after the implantable transducer system is positioned in the cannular cavity so as to secure the transducer within the cannular cavity.

BRIEF DESCRIPTION OF THE DRAWINGS

Embodiments of the present invention are described herein in conjunction with the accompanying drawings, in which.

DETAILED DESCRIPTION

Presented herein are implantable transducer systems for implantable hearing prostheses. The implantable transducer systems in accordance with embodiments presented herein include a transducer, such as an actuator or sensor (e.g., microphone), and an expandable fixation arrangement, such as a radially expandable fixation arrangement, that is configured to anchor/secure the implantable transducer system directly within an elongate cannular cavity extending through a portion of a recipient's skull bone. The implantable transducer system may be used with implantable acoustic auditory prostheses (i.e., to secure an actuator within a recipient) or with implantable stimulating auditory prostheses, such as cochlear implant (i.e., to secure a microphone within a recipient).

Figure 1:
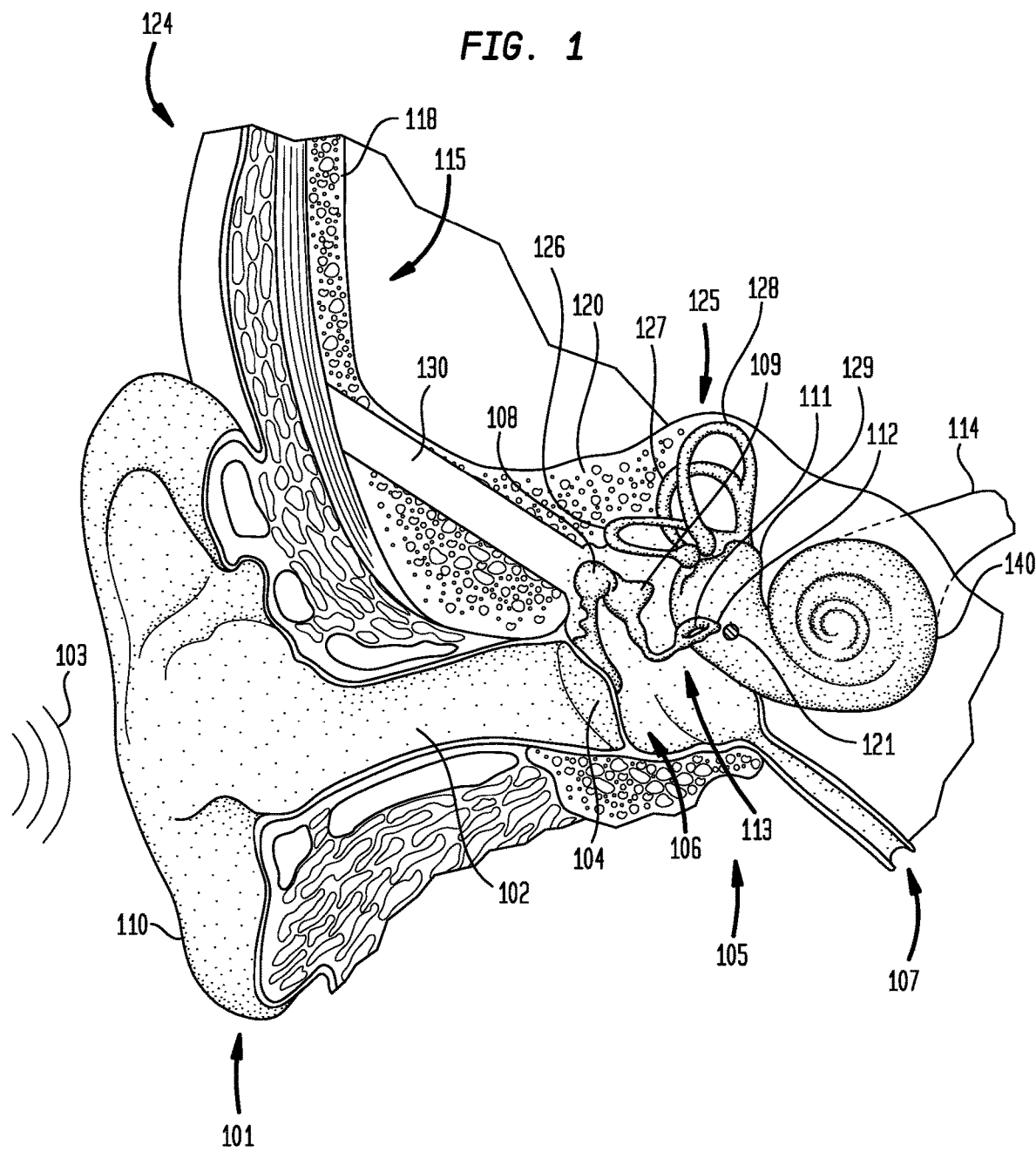
FIG. 1 is a schematic diagram illustrating the anatomy of a recipient at a location in which an implantable transducer system in accordance with embodiments presented herein may be implanted.

Before describing illustrative embodiments of the implantable transducer systems presented herein, a brief description of the human anatomy of a recipient's ear is first provided with reference to FIG. 1. More specifically, shown in FIG. 1 illustrates a recipient's outer ear 101, middle ear 105, and inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121, through the bones of the middle ear 105. The bones of the middle ear 105 comprise the malleus 108, the incus 109 and the stapes 111, collectively referred to as the ossicles 106. The ossicles 106 are positioned in the middle ear cavity 113 and serve to filter and amplify the sound wave 103, causing oval window 112 to articulate (vibrate) in response to the vibration of tympanic membrane 104. This vibration of the oval window 112 sets up waves of fluid motion of the perilymph within the cochlea 140, which forms part of the inner ear 107. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound The human skull is formed from a number of different bones that support various anatomical features. Illustrated in FIG. 1 is the temporal bone 115 which is situated at the side and base of the recipient's skull 124. For ease of reference, the temporal bone 115 is referred to herein as having a superior portion 118 and a mastoid portion 120. The superior portion 118 comprises the section of the temporal bone 115 that extends superior to the auricle 110. That is, the superior portion 118 is the section of the temporal bone 115 that forms the side surface of the skull. The mastoid portion 120, referred to herein simply as the mastoid 120, is positioned inferior to the superior portion 118. The mastoid 120 is the section of the temporal bone 115 that surrounds the middle ear 105.

As shown in FIG. 1, semicircular canals 125 are three half-circular, interconnected tubes located adjacent cochlea 140. The semicircular canals 125 also form part of the inner ear 107 and are in fluid communication with the cochlea 140 via the vestibule 129. The three semicircular canals comprise the horizontal semicircular canal 126, the posterior semicircular canal 127, and the superior semicircular canal 128. The canals 126, 127 and 128 are aligned approximately orthogonally to one another. Specifically, when the individual is in an upright position, the horizontal canal 126 is aligned roughly horizontally in the head, while the superior 128 and posterior canals 127 are aligned roughly at a 45 degree angle to a vertical through the center of the individual's head.

Each semicircular canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

As noted, embodiments of the present invention are directed to implantable transducer systems configured to be implanted in an elongate channel (cannular cavity) formed in a recipient's skull bone in order deliver vibration to at least one element of a recipient's ear. FIG. 1 illustrates a cannular cavity 130 formed in the mastoid portion 120 of the temporal bone 115 in which an implantable actuator in accordance with embodiments presented herein. In general, the cannular cavity 130 is a drilled channel formed through the use of a drilling tool (not shown in FIG. 1). During the drilling process, the drilling tool may be manually guided or computer guided (e.g., a computer guided surgery). The implantation of an implantable transducer system in accordance with embodiments presented herein into the small cannular cavity 130 extending to the middle ear cavity eliminates the need to create a large mastoidectomy used in conventional arrangements and, accordingly, reduces trauma associated with the implantation process. The fixation arrangements presented herein advantageously reduce surgery time as the implantable transducer system can be quickly anchored within the cannular cavity. For ease of illustration, FIG. 1 shows the cannular cavity 130 without an implantable transducer system disposed therein.

Figure 2A:
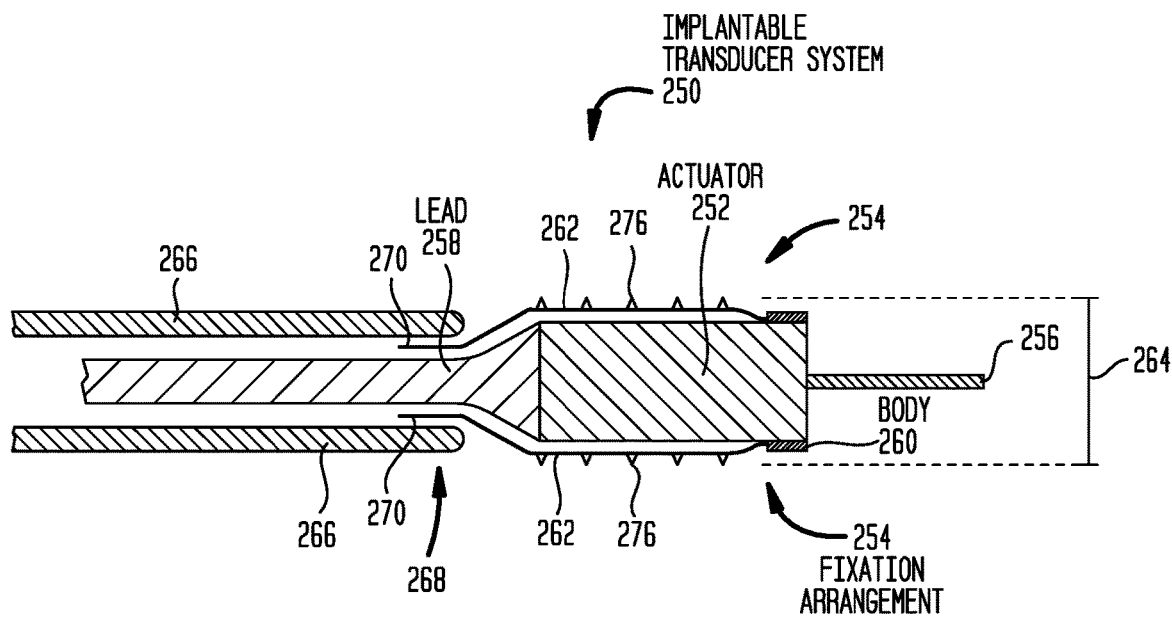
FIGS. 2A, 2B, and 2C are cross-sectional views of an implantable transducer system in accordance with embodiments presented herein.
Figure 2B:
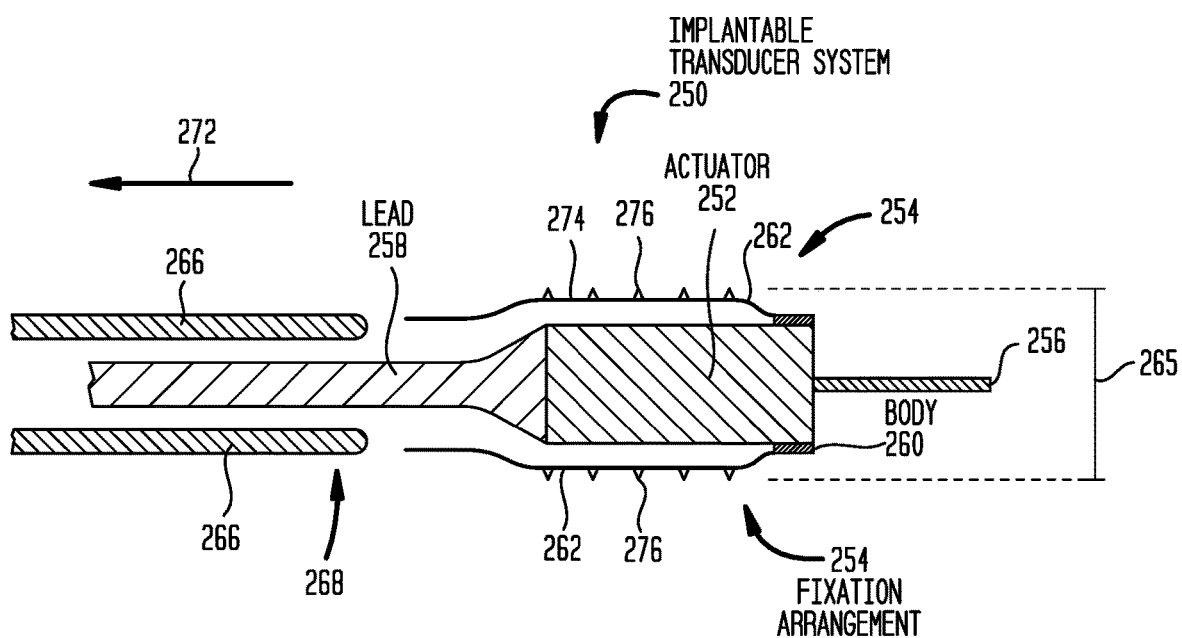
Figure 2C:
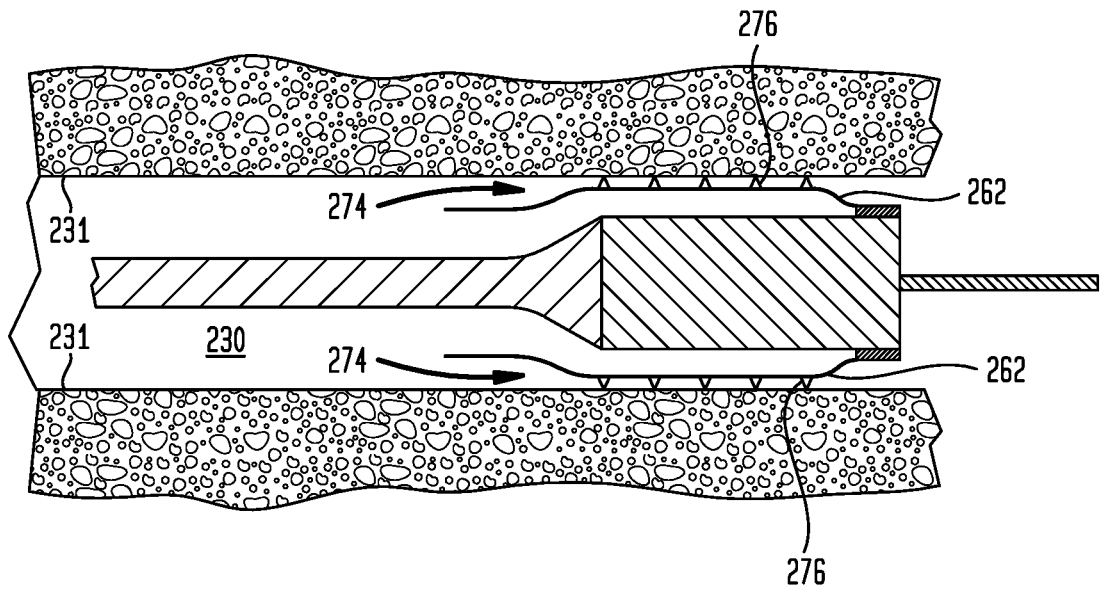
Figure 2D:
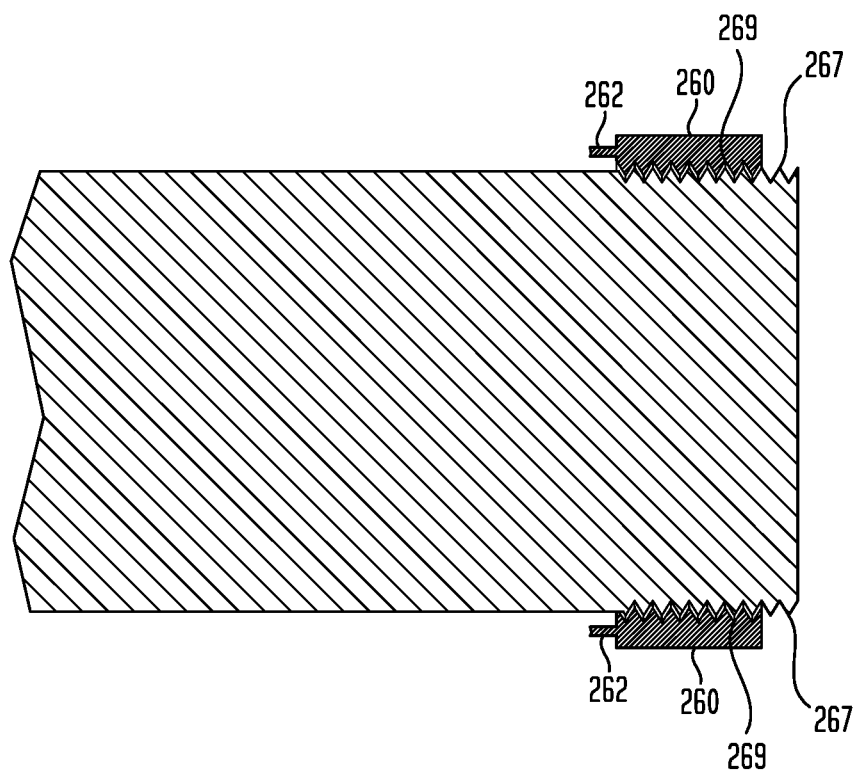
FIG. 2D is an enlarged cross-sectional view of a portion of the implantable transducer system of FIG. 2A.

FIGS. 2A-2C are cross-sectional views of an implantable transducer system 250 that includes an example transducer in the form of an actuator 252 and an integrated radially expandable fixation arrangement 254 in accordance with embodiments presented herein. FIG. 2D is an enlarged cross-sectional view of a portion of the implantable transducer system of FIGS. 2A-2C.

As described elsewhere herein, implantable transducer systems in accordance with embodiments presented herein may be used with (i.e., as part of) a number of different implantable acoustic auditory prostheses, such as middle ear auditory prostheses, direct acoustic stimulators, etc. In these arrangements, the transducer is a sensor (e.g., microphone) that is configured to detect sound signals, body noise, etc. Implantable transducer systems in accordance with embodiments presented herein may be used with (i.e., as part of) a number of different implantable stimulating auditory prostheses, such as cochlear implants, auditory brainstem stimulators, etc. In these arrangements, the transducer is an actuator that is configured to deliver mechanical forces (vibrations) to the recipient. Merely for ease of illustration, the examples of FIGS. 2A-2D are described with reference to a transducer comprising an actuator.

The implantable transducer system 250 is a component of a partially or fully implantable acoustic auditory prosthesis, such as a middle ear auditory prosthesis (middle ear implant) or direct acoustic stimulator (direct cochlear stimulator), configured to deliver vibrations to a recipient in order to directly or indirectly generate movement of the cochlea fluid. As such, the actuator 252 includes an interface (e.g., rod) 256 that is configured to be coupled to an anatomical structure of the recipient's ear, such as the oval window 112, the round window 121, the ossicles 106, etc.

In addition to the implantable transducer system 250, an implantable acoustic auditory prosthesis may include, among other elements, a power source (e.g., one or more batteries), one or more sound input elements (e.g., microphones, telecoils, etc.) for receiving sound signals, and a sound processor configured to process electrical signals generated by the sound input element (i.e., convert the electrical signals into actuator drive signals). These various other elements may be implanted in the recipient or housed in an external component configured to be worn by the recipient. FIGS. 2A and 2B generally illustrate a lead 258 extending from the actuator 252 for connection to these or other components of the middle ear auditory prosthesis.

As noted, the implantable transducer system 250 includes the radially expandable fixation arrangement 254 that is configured to anchor/secure the actuator 252 directly within an elongate channel (cannular/tubular cavity) formed in a recipient's skull bone (i.e., substantially prevent withdrawal or movement of the implantable transducer system without surgical intervention). For ease of illustration, FIGS. 2A and 2B illustrate the implantable transducer system 250 separate from any cannular cavity. However, FIG. 2C illustrates the implantable transducer system 250 disposed in a cannular cavity in which the expandable fixation arrangement 254 is deployed/expanded.

The expandable fixation arrangement 254 comprises a body 260 that is connected to a distal end of the actuator 252. Extending from the body 260 are a plurality of expansion or leaf blades 262 that, as shown in FIG. 2A, have an initial compressed configuration to enable the implantable transducer system 250 to be inserted into the cannular cavity. That is, the expandable fixation arrangement 254 has an initial outer dimension (e.g., width, diameter, etc.) 264 during insertion into the cannular cavity. As shown in FIG. 2A, the leaf blades 262 are retained in the initial compressed configuration by an insertion tool 266. The insertion tool 266 is an elongate instrument having a distal end 268 configured to engage and force a proximal end 270 of each of the leaf blades 262 inward (i.e., toward the actuator 252 and/or the lead 258).

Once the implantable actuator 252 is located at a selected/desired location within the cannular cavity, the insertion tool 266 is withdrawn in a proximal direction 272 so that the distal end 268 disengages from (i.e., releases) the proximal ends 270 of the leaf blades 262. The leaf blades 262 have a shape and material properties such that, once released by the insertion tool 266, one or more portions of the leaf blades 262 will expand outward from the actuator 252 to a final expanded configuration. That is, the leaf blades 262 spring outward or away from the actuator 252 and, once expanded, the leaf blades 262 have a final outer dimension 265. The final outer dimension 265 is larger than the initial outer dimension 264.

In certain embodiments, the leaf blades 262 may be formed from, for example, a biocompatible metal (e.g., titanium). In one specific arrangement, the leaf blades 262 are each formed from a memory material (e.g., nitinol) that is configured to expand after insertion of the implantable transducer system 250 into the cannular cavity in response to the recipient's body temperature.

As shown in FIG. 2C, when the leaf blades 262 are released and to their expanded configuration, an outer surface 274 of each of the leaf blades 262 is configured to engage the inner surface 231 of an elongate cannular cavity 230. As a result of the engagement between the outer surface 274 of each of the leaf blades 262, the position of the actuator system 250 is fixed within the cannular cavity 230.

In the embodiments of FIGS. 2A-2C, the outer surface 274 of each of the leaf blades 262 includes surface features in the form of hook-shaped elements 276 that are configured to grip the inner surface 231 of the cannular cavity 230 (i.e., grip the bone surrounding the cavity). These surface features 276 serve to increase the increase the friction between the outer surface 274 of the leaf blades 262 and the inner surface 231 to further prevent movement of the actuator system 250.

As noted above, FIGS. 2A-2C are cross-sectional views of the implantable transducer system 250 that, in general, illustrates two (2) leaf blades 262. It is to be appreciated that the illustration of two leaf blades is a result of the cross-sectional view and that embodiments of the present invention may include more than two leaf blades. In certain embodiments, the leaf blades substantially surround the actuator 252.

In accordance with embodiments presented herein, the body 260 may be attached to the actuator 252 in a number of different manners. For example, FIG. 2D illustrates one example arrangement in which any inner surface 269 of the body 262 and an outer surface 267 of a distal portion 271 of the actuator 252 have corresponding screw threads. Due to this threaded engagement between the body 262 and the actuator 252, the longitudinal location of the actuator 252 may be adjusted relative to the fixation arrangement 254. The ability to move the actuator 252 relative to the fixation arrangement 254 facilitates fine adjustments so that the interface 256 can be appropriately coupled to an anatomical structure of the recipient's ear. In certain embodiments, the interface 256 may also or alternatively be adjustable to facilitate fine positioning (e.g., through the inclusion of Z-translation screws or other integrated fine positioning mechanism).

Figure 3:
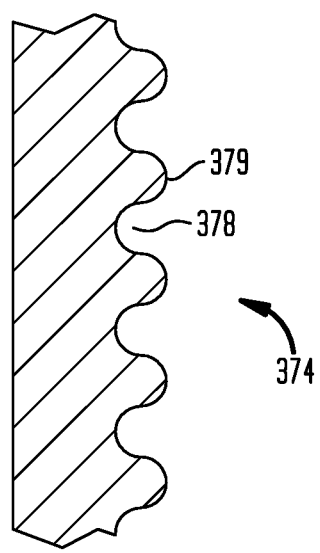
FIG. 3 is a cross-sectional view of surface features that may be disposed on a portion of a radially expandable fixation arrangement in accordance with embodiments presented herein.

Also as noted, FIGS. 2A-2C illustrate surface features in the form of hook-shaped elements 276. It is to be appreciated that these specific surface features are illustrative and that leaf blades, or other fixation arrangements in accordance with embodiments presented herein, may include alternative surface features. For example, FIG. 3 is a cross-sectional view of a portion of a surface 374 a radially expandable fixation arrangement (e.g., a portion of an outer surface of a leaf blade) that includes surface features comprising spaced grooves/troughs 378 separated by ridges 379. The grooves 378 are, in this embodiment, elongate concave grooves having a radius of curvature and extending substantially across the surface 374. Similarly, the ridges 379 are elongate convex ridges having a radius of curvature and which extend substantially across the surface 374. In general, the grooves 378 and ridges 379 function to increase the surface area of the surface 374 (relative to a planar surface) so as to increase the friction between the surface 374 and a recipient's skull bone surrounding a cannular cavity in which an implantable transducer system in accordance with embodiments presented here may be implanted.

As noted, FIG. 3 illustrates embodiments where the grooves 378 and ridges 379 extend substantially across the surface 374. It is to be appreciated that in alternative embodiments the grooves 378 and ridges 379 only extend across one or more portions of the surface 374 to form a symmetrical or an asymmetrical arrangement of grooves/ridges.

FIG. 3 illustrates a specific implementation where grooves 378 are used in combination with ridges 379. In certain embodiments, the grooves 378 are formed through the creation of ridges 379 or vice versa. It is also to be appreciated that other embodiments of surface 374 include only grooves 378 or only ridges 379.

FIG. 3 illustrates an exemplary arrangement for grooves in accordance with embodiments presented herein. It is also to be appreciated that grooves in alternative embodiments may have different geometries. For example, alternative grooves may be T-square-shaped, shaped, J-shaped, dovetailed, frustoconical, etc.

Figure 4A:
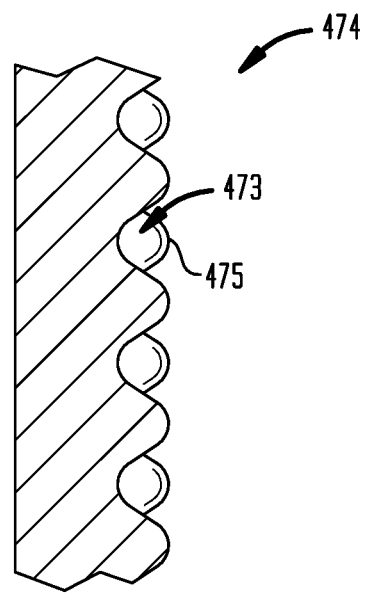
FIG. 4A is a cross-sectional view of surface features that may be disposed on a portion of a radially expandable fixation arrangement in accordance with embodiments presented herein.
Figure 4B:
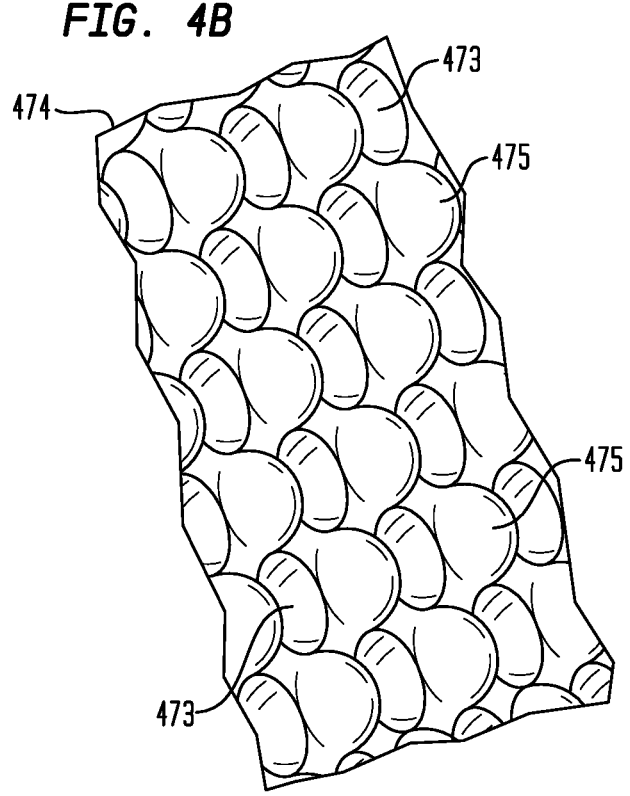
FIG. 4B is a perspective view of surface features that may be disposed on a portion of a radially expandable fixation arrangement in accordance with embodiments presented herein.

FIGS. 4A and 4B are cross-sectional and perspective views, respectively, of a portion of a surface 474 of a portion of a radially expandable fixation arrangement (e.g., an outer surface of a leaf blade) that includes surface features comprising a plurality of depressions 473 spaced between protrusions 475. The protrusions 475 have, as shown in FIGS. 4A and 4B, a generally parabolic or dome shape and are disposed across the surface 474. In general, the protrusions 475 function to increase the surface area of the surface 474 (relative to a planar surface) so as to increase the friction between the surface 474 and a recipient's skull bone surrounding a cannular cavity in which an implantable transducer system in accordance with embodiments presented herein is implanted.

Figure 5A:
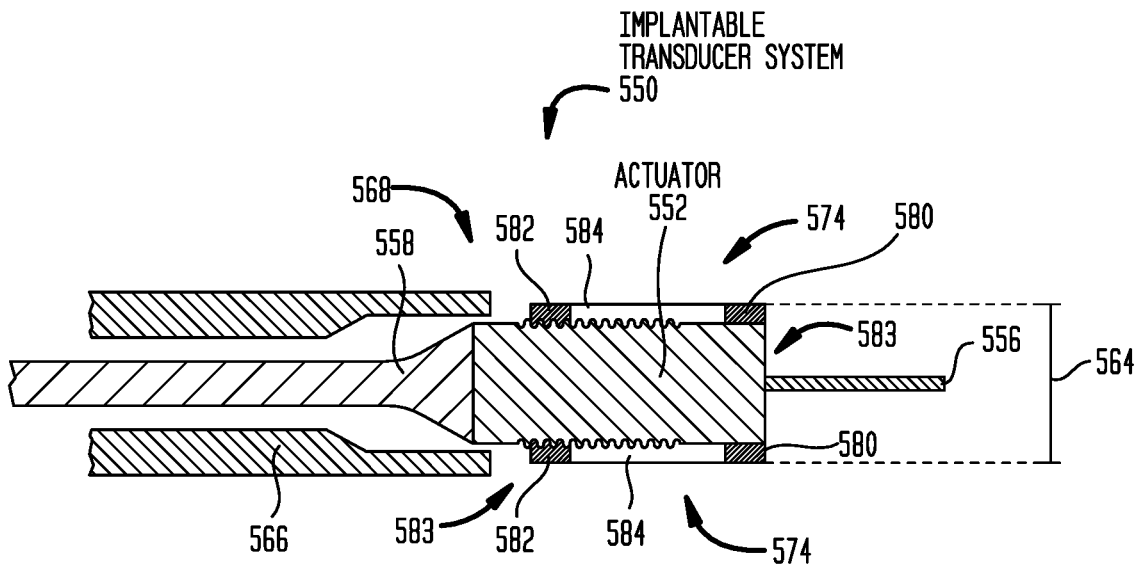
FIGS. 5A, 5B, and 5C are cross-sectional views of an implantable transducer system in accordance with embodiments presented herein.
Figure 5B:
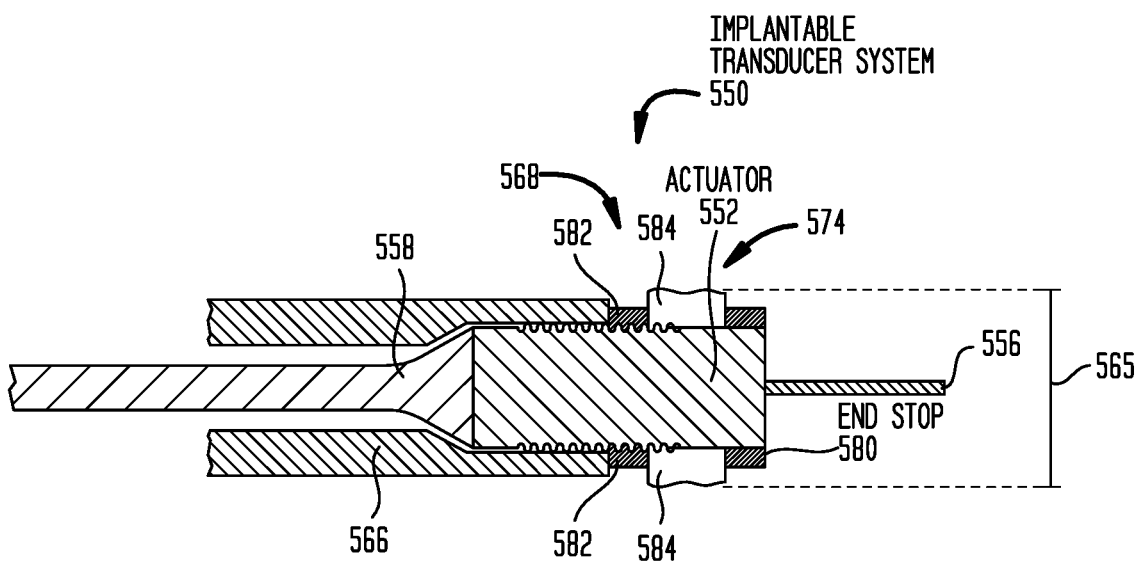
Figure 5C:
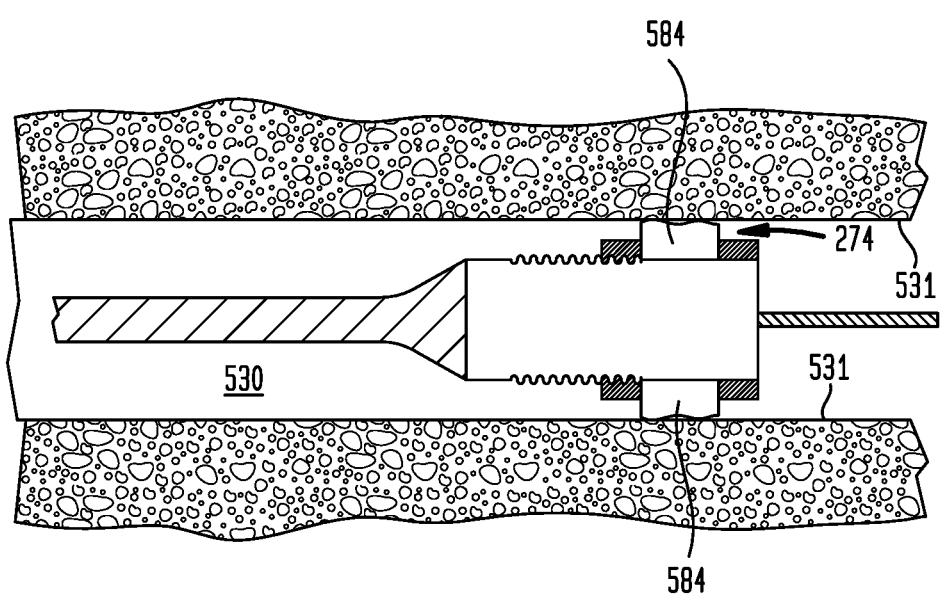

FIGS. 5A-5C are cross-sectional views of another embodiment of an implantable transducer system 550 in accordance with embodiments presented herein that includes an actuator 552 and an integrated radially expandable fixation arrangement 554. As described elsewhere herein, implantable transducer systems in accordance with embodiments presented herein may be used with (i.e., as part of) a number of different implantable acoustic auditory prostheses, such as middle ear auditory prostheses, direct acoustic stimulators, etc. In these arrangements, the transducer is a sensor (e.g., microphone) that is configured to detect sound signals, body noise, etc. Implantable transducer systems in accordance with embodiments presented herein may be used with (i.e., as part of) a number of different implantable stimulating auditory prostheses, such as cochlear implants, auditory brainstem stimulators, etc. In these arrangements, the transducer is an actuator that is configured to deliver mechanical forces (vibrations) to the recipient. Merely for ease of illustration, the examples of FIGS. 5A-5C are described with reference to a transducer comprising an actuator.

Similar to the embodiments of FIGS. 2A-2D, the implantable transducer system 550 may be a component of a partially or fully implantable acoustic auditory prosthesis, such as a middle ear auditory prosthesis (middle ear implant) or direct acoustic stimulator (direct cochlear stimulator), configured to deliver vibrations to a recipient so as to directly or indirectly generate movement of the cochlea fluid. As such, the actuator 552 includes an interface (e.g., rod) 556 that is configured to be coupled to an anatomical structure of the recipient's ear, such as the oval window 112, the round window 121, the ossicles 106, etc. As noted above, such an implantable acoustic auditory prosthesis may also include, among other elements, a power source, one or more sound input elements, and a sound processor. FIGS. 5A-5C generally illustrate a lead 558 extending from the actuator 552 for connection to these or other components of the middle ear auditory prosthesis.

As noted, the implantable transducer system 550 includes the radially expandable fixation arrangement 554 that is configured to secure the actuator 552 directly within an elongate channel (cannular/tubular cavity) formed in a recipient's skull bone. For ease of illustration, FIGS. 5A and 5B illustrate the implantable transducer system 550 separate from a cannular cavity. However, FIG. 5C illustrates the implantable transducer system 550 disposed in a cannular cavity in arrangement in which the expandable fixation arrangement 554 is deployed/expanded.

The expandable fixation arrangement 554 comprises an end stop 580 that is attached to the distal region 583 of the actuator 552, a moveable member 582 coupled to a proximal region 584 of the actuator 552, and an expansion member 584. As shown in FIG. 5A, the expansion member 584 has an initial compressed configuration to enable the implantable transducer system 550 to be inserted into the cannular cavity. That is, the expansion member 584, and more generally the expandable fixation arrangement 554, has an initial outer dimension 564 during insertion into the cannular cavity.

As shown in FIG. 5B, once the implantable actuator 552 is located at a selected/desired location within the cannular cavity, the moveable member 582 is advanced/moved along actuator 552 in a distal direction (i.e., towards the distal region 582). As a result of the advancement of the moveable member 582, the expansion member 584 is placed under compressive force exerted by both the moveable member 582 and the end stop 580 attached to the actuator 552. When placed under compression, the expansion member 584 is configured to expand outward from the actuator 552 to a final expanded configuration. That is, the expansion member 584 is compressed outward or away from the actuator 552 so as to have a final outer dimension 565 that is larger than the initial outer dimension 564.

The moveable member 582 is advanced through application of force by an insertion tool 566. The insertion tool 566 is an elongate instrument having a distal end 568 configured to engage a proximal end of the moveable member 582. In certain embodiments, the moveable member 582 and the outer surface of the actuator 552 have corresponding screw threads such that the moveable member 582 is advanced through a screwing motion. After the expansion member 584 reaches its final expanded configuration, the distal end 568 of the insertion tool 566 is disengaged from the moveable member 582 and the insertion tool 566 is withdrawn from the cannular cavity.

As shown in FIG. 5C, when the expansion member 584 is expanded, an outer surface 574 of the expansion member 584 is configured to engage an inner surface 531 of an elongate cannular cavity 530. As a result of the engagement between the outer surface 574 with the inner surface 531, the position of the moveable member 582, and thus the actuator system 550 is fixed within the cannular cavity 530. In other embodiments, a bracket or other locking member may also be positioned at the proximal end of the moveable member 582 to prevent proximal migration/drift of the moveable member 582 and the actuator system 550.

Once disengaged from the insertion tool, the moveable member 582 may be configured to remain in the set location by itself. For example, the threaded engagement between the moveable member 582 and the outer surface of the actuator 552 may be sufficient to retain the moveable member at the set location. In other examples, a bracket or other locking member may also be positioned at the proximal end of the moveable member 582 to prevent proximal migration/drift of the moveable member 582. In a still other embodiment, a biocompatible adhesive may be applied to the interface between the moveable member 582 and the outer surface of the actuator 552 to lock the moveable member 582 at the set location.

In general, the expansion member 584 is formed from a resiliently flexible material (e.g., silicone). In addition to securing the actuator system 550 within the recipient, a resiliently flexible expansion member 584 may also operate to isolate the actuator 552 from body noises.

In the embodiments of FIGS. 5A-5C, the outer surface 574 of the expansion member 584 includes surface features in the form of a textured surface that is configured to grip the inner surface 531 of an elongate cannular cavity 530 (i.e., grip the bone surrounding the cavity). These surface features serve to increase the increase the friction between the outer surface 574 of the expansion member 584 with the inner surface 531 of further prevent movement of the actuator system 550. The outer surface 574 of the expansion member 584 may include any of the surface features shown in FIGS. 2A-2C, 3, 4A-4B, or other surface features.

FIGS. 5A-5C have been described with reference to a circumferential expansion member 584 that is compressed between a circumferential moveable member 582 and a circumferential end stop 580. It is to be appreciated that the use of circumferential elements is illustrative and that other embodiments may make use of multiple discrete expansion members with one or more moveable members and/or end stops.

FIGS. 5A-5C have also been described with reference to an expansion member 584 that expands outward in response to compressive forces. It is to be appreciated that, in alternative embodiments, the expansion member 584 may be formed from a shape memory metal that is configured to expand in response to a temperature change induced by the recipient's body temperature. Alternatively, the expansion member 584 may be formed from a material that is configured to swell when exposed to the recipient's bodily fluid.

Figure 6:
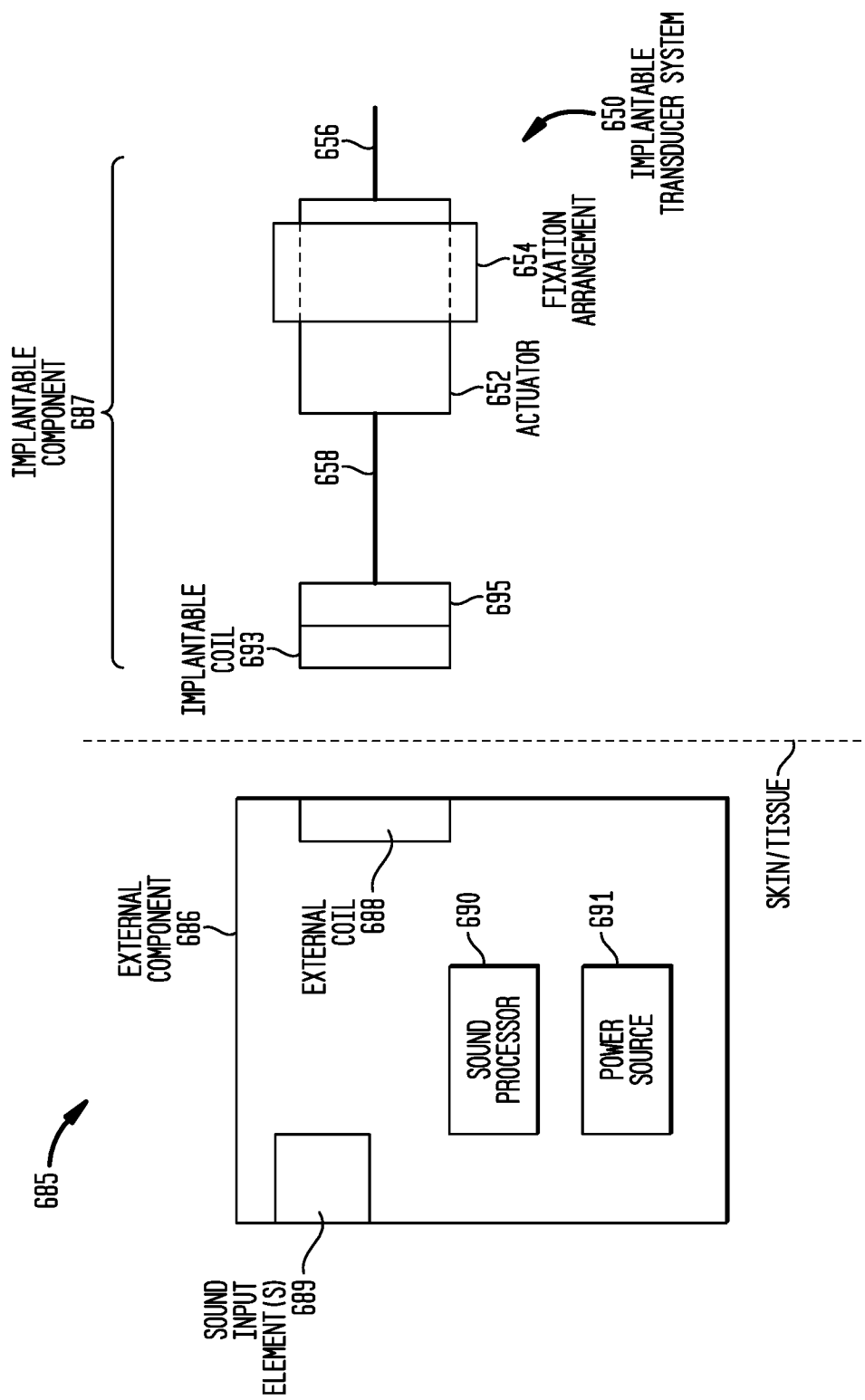
FIG. 6 is a block diagram of an implantable auditory prosthesis comprising an implantable transducer system in accordance with embodiments presented herein.

FIG. 6 is a block diagram illustrating an implantable auditory prosthesis 685 that includes an implantable transducer system 650 comprising an integrated radially expandable fixation arrangement 654 in accordance with embodiments presented herein. The implantable auditory prosthesis 685 includes an external component 686 and an implantable component 687. The external component 686 is directly or indirectly attached to the body of the recipient and typically comprises an external coil 688 and, generally, a magnet (not shown) fixed relative to the external coil. The external component 686 also comprises one or more sound input elements 689 (e.g., microphones, telecoils, etc.) for receiving sound signals, a sound processor 690, and a power source 691 (e.g., battery).

The implantable component 687 comprises an implantable coil 693 and, generally, a magnet (not shown) fixed relative to the implantable coil 693. The magnets adjacent to the external coil 688 and the implantable coil 693 facilitate the operational alignment of the external and implantable coils. The operational alignment of the coils enables the external coil 688 to transcutaneously transmit power and data to, and possibly receive data from, the implantable coil 693.

The implantable component 687 also comprises an electronics assembly 695 and the implantable transducer system 650 that is electrically connected to the electronics assembly 695 via a lead 658. The implantable transducer system 650 comprises an actuator 652 and a radially expandable fixation arrangement 654 that, similar to the above embodiments, is configured to secure the implantable transducer system 650 within a cannular cavity formed in a recipient's skull bone.

In operation, the sound processor 689 is configured to process electrical signals generated by the sound input element 688. In other words, the sound processor 689 converts the electrical signals into data signals that encoded and transferred to the implantable component 687 via the coils 688 and 693. The electronics assembly 695 uses the data received from the external component 686 to generate electrical signals (drive signals) that are delivered to actuator 652. When delivered to the actuator 652, the drive signals cause the actuator 652 to generate vibration which is transferred through a recipient's tissue and/or bone to the cochlea via an interface 656, thereby causing generation of nerve impulses that result in the perception of the sound signals received by the sound input element(s) 689.

As noted, FIG. 6 illustrates an example in which the implantable auditory prosthesis 685 includes an external component 686 with an external sound processor. It is to be appreciated that the use of an external component is merely illustrative and that the techniques presented herein may be used in arrangements having an implanted sound processor, an implanted microphone, and/or an implanted power source (battery). It is also to be appreciated that the individual components referenced herein, e.g., sound input elements, the sound processor, etc., may be distributed across more than one device, e.g., two middle ear auditory prostheses, and indeed across more than one type of device, e.g., a middle ear auditory prosthesis and a consumer electronic device or a remote control of the middle ear auditory prosthesis.

FIGS. 7A-7C and 8 are diagrams illustrating alternative mechanisms for fixing an implantable transducer system in a drilled channel by screw threads, to be operated by a screw tool (e.g., a dedicated tool or an off the shelf screwdriver) so that the implantable transducer system may be secured directly within the channel via only a screwing action.

Figure 7A:
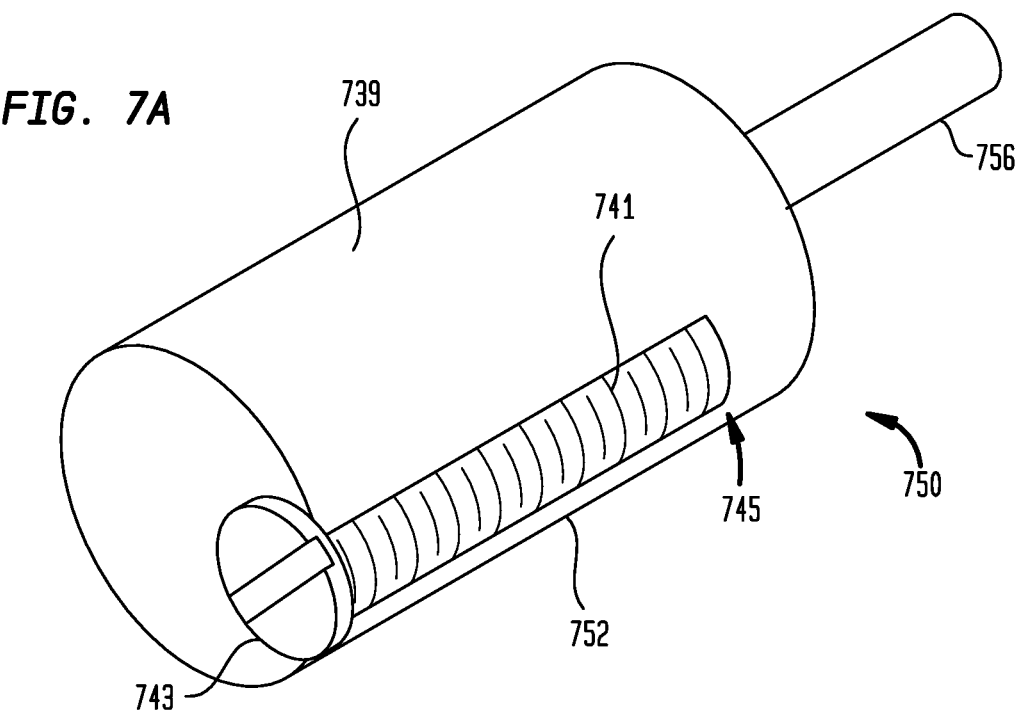
FIG. 7A is a perspective view of an implantable transducer system in accordance with embodiments presented herein.
Figure 7B:
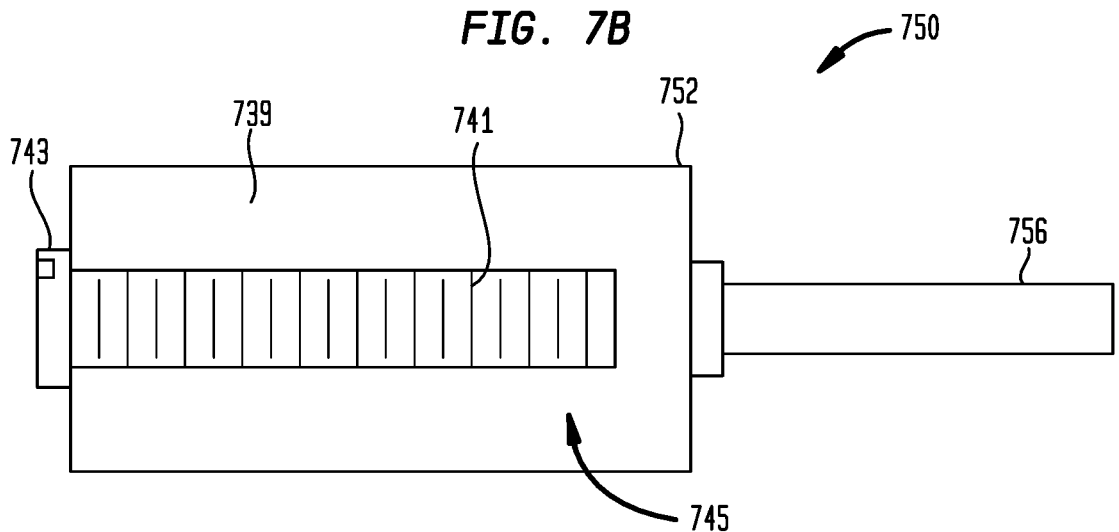
FIG. 7B is a side view of the implantable transducer system of FIG. 7A.
Figure 7C:
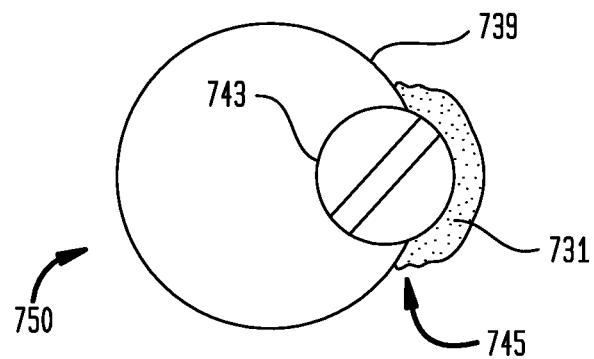
FIG. 7C is a side view of the implantable transducer system of FIG. 7A.

More specifically, FIGS. 7A, 7B, and 7C are perspective, side, and rear views, respectively, of an implantable transducer system 750 in accordance with examples presented herein. The implantable transducer system 750 comprises an actuator 752 having an exterior surface 739 and an interface (e.g., rod) 756 that is configured to be coupled to an anatomical structure of the recipient's ear. Protruding from the exterior surface 739 is a threaded fixation mechanism 745 comprising a threaded portion 741 and a screw head 745. The screw head 745 is configured to be operated by a screw tool (e.g., a dedicated tool or an off the shelf screwdriver) so that the protruding threaded portion 741 (screw threads) grip into the bone 731 surrounding a drilled channel. The arrangement shown in FIGS. 7A, 7B, and 7C may be used alone to secure an implantable transducer system 750 within the recipient or may be used in combination with, for example, the embodiments of FIG. 2A-2D or 5A-5C.

Figure 8:
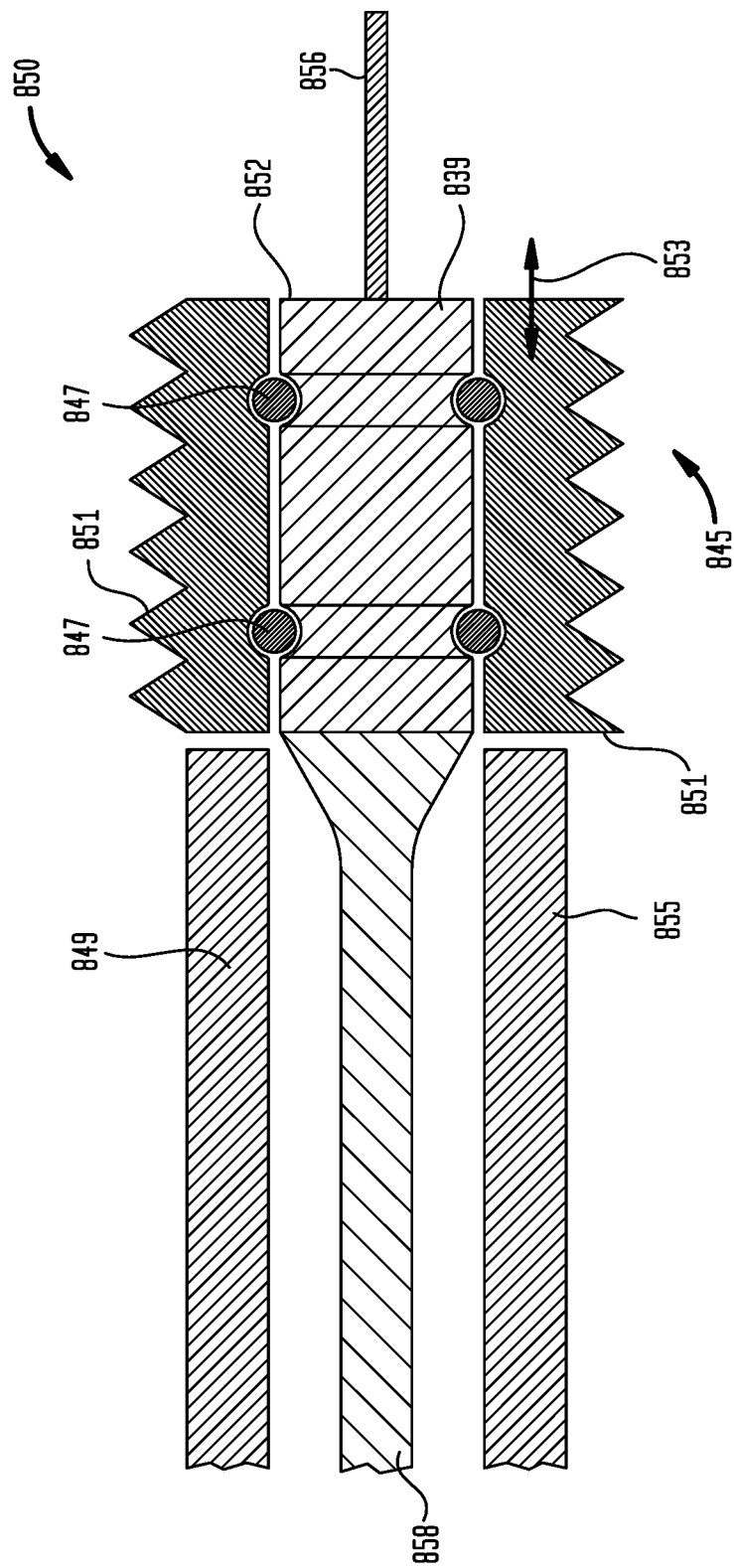
FIG. 8 is a sectional side view of an implantable transducer system in accordance with embodiments presented herein.

FIG. 8 is a sectional side view of an implantable transducer system 850 in accordance with examples presented herein. The implantable transducer system 850 comprises an actuator 852 having an exterior surface 839 and an interface (e.g., rod) 856 that is configured to be coupled to an anatomical structure of the recipient's ear. Disposed around the exterior surface 839 is a threaded fixation mechanism 845 that comprises a self-tapping threaded body 851 and ball bearings 847. A proximal end 870 of the threaded body 851 is configured to be operated by a screw tool 855 so that the threaded body 851 (screw threads) grips into bone (not shown) surrounding a drilled channel. The ball bearings 847 enable rotation of the threaded body 851 that is independent from the actuator 852. That is, the ball bearings 847 enable the threaded body 851 to rotate around the actuator 852, while the actuator 852 does not rotation. This prevents rotation or twisting of the lead 858 attached to the actuator 852. Through the screwing action, the implantable transducer system 850 may be moved both forward and backwards, as shown by bi-directional arrow 853.

As noted above, implantable transducer systems in accordance with embodiments presented herein may be used with (i.e., as part of) a number of different implantable acoustic auditory prostheses, such as middle ear auditory prostheses, direct acoustic stimulators, etc. In these arrangements, the transducer is a sensor (e.g., microphone) that is configured to detect sound signals, body noise, etc. Implantable transducer systems in accordance with embodiments presented herein may be used with (i.e., as part of) a number of different implantable stimulating auditory prostheses, such as cochlear implants, auditory brainstem stimulators, etc. In these arrangements, the transducer is an actuator that is configured to deliver mechanical forces (vibrations) to the recipient.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable transducer system, comprising:
   an implantable transducer configured for insertion into a cannular cavity formed in a recipient; and
   a fixation arrangement attached to the implantable transducer, wherein the fixation arrangement comprises at least one radially expandable member configured to, following insertion into the cannular cavity, expand outward from the implantable transducer to exert a transverse force on an inner surface defining the cannular cavity to anchor the implantable transducer at a location within the cannular cavity,
   wherein the fixation arrangement is coupled to the implantable transducer so as to permit longitudinal movement of the transducer relative to the fixation arrangement.

2. The implantable transducer system of claim 1, wherein the fixation arrangement comprises a body coupled to a distal end of the implantable transducer; and wherein the at least one radially expandable member comprises a plurality of leaf blades extending from the body in a generally proximal direction,
   wherein following insertion into the cannular cavity, the leaf blades are configured to expand outward from the implantable transducer in order to exert the transverse force on the inner surface defining the cannular cavity.

3. The implantable transducer system of claim 2, wherein each of the plurality of leaf blades has a proximal end configured to engage an insertion tool that retains a proximal end of each of the plurality of leaf blades in a compressed configuration during insertion of the implantable transducer into the cannular cavity.

4. The implantable transducer system of claim 2, wherein each of the plurality of leaf blades is formed from a memory material configured to expand after insertion of the implantable transducer into the cannular cavity in response to the recipient's body temperature.

5. The implantable transducer system of claim 1, wherein an outer surface of the implantable transducer and an inner surface of the fixation arrangement have corresponding screw threads so as permit longitudinal movement of the implantable transducer relative to the fixation arrangement.

6. The implantable transducer system of claim 1, wherein an outer surface of fixation arrangement includes surface features configured to increase friction between the fixation arrangement and the inner surface defining the cannular cavity.

7. The implantable transducer system of claim 1, wherein the fixation arrangement comprises:
   at least one end stop connected to a distal end of the implantable transducer;
   at least one moveable member coupled to an outer surface of the implantable transducer; and
   wherein the at least one radially expandable member comprises at least one expansion member disposed between the at least one end stop and the at least one moveable member,
   wherein the at least one moveable member is configured to be advanced along the outer surface of the implantable transducer in a distal direction to place the at least one expansion member under compressive force exerted by both the at least one moveable member and the at least one end stop such that the at least one expansion member expands outward from the surface of the implantable transducer in order to exert the transverse force on the inner surface defining the cannular cavity.

8. The implantable transducer system of claim 7, wherein the at least one moveable member is configured to be advanced in the distal direction through application of force by an insertion tool.

9. The implantable transducer system of claim 7, wherein the outer surface of the implantable transducer and an inner surface of the at least one moveable member have corresponding screw threads so as permit distal movement of the at least one moveable member along the outer surface of the implantable transducer.

10. The implantable transducer system of claim 7, wherein the at least one expansion member is a circumferential expansion member substantially surrounding a section of an outer surface of the implantable transducer.

11. The implantable transducer system of claim 7, wherein an outer surface of the at least one expansion member includes surface features configured to increase friction between the at least one expansion member and the inner surface defining the cannular cavity.

12. The implantable transducer system of claim 1, wherein the implantable transducer is an actuator.

13. The implantable transducer system of claim 1, wherein the implantable transducer is a microphone.

14. An implantable hearing prosthesis comprising the implantable transducer system of claim 1.

15. An implantable transducer system configured to be positioned in a cannular cavity formed in a recipient, comprising:
   an implantable transducer; and
   a fixation arrangement coupled to the implantable transducer and comprising at least one expandable member having a first compressed configuration to facilitate insertion into the cannular cavity and configured to expand, following insertion of the implantable transducer system into the cannular cavity, to a second expanded configuration so as to exert an outward force on a wall of the cannular cavity to secure the implantable transducer within the cannular cavity,
   wherein a longitudinal location of the implantable transducer relative to the fixation arrangement is adjustable.

16. The implantable transducer system of claim 15, wherein the at least one expandable member comprises at least one radially expandable member.

17. The implantable transducer system of claim 15, wherein the at least one expandable member comprises:
a plurality of leaf blades attached to a distal end of the implantable transducer and each extending in a generally proximal direction,
wherein following insertion into the cannular cavity, each of the plurality of leaf blades is configured to expand outward from the implantable transducer in order to exert an independent outward force on the wall of the cannular cavity.

18. The implantable transducer system of claim 17, wherein each of the plurality of leaf blades has a proximal end configured to engage an insertion tool that retains a proximal end of each of the plurality of leaf blades in a compressed configuration during insertion of the implantable transducer into the cannular cavity.

19. The implantable transducer system of claim 17, wherein each of the plurality of leaf blades is formed from a memory material configured to expand after insertion of the implantable transducer into the cannular cavity in response to the recipient's body temperature.

20. The implantable transducer system of claim 15, wherein the fixation arrangement further comprising at least one end stop connected to a distal end of the implantable transducer and at least one moveable member coupled to an outer surface of the implantable transducer, and wherein the at least one expandable member comprises:
a resiliently flexible member disposed between the at least one end stop and the at least one moveable member,
wherein the at least one moveable member is configured to be advanced along the outer surface of the implantable transducer in a distal direction to place the resiliently flexible member under compressive force exerted by both the at least one moveable member and the at least one end stop such that the resiliently flexible member expands outward from the surface of the implantable transducer in order to exert an independent outward force on the wall of the cannular cavity.

21. The implantable transducer system of claim 20, wherein the at least one moveable member is configured to be advanced in the distal direction through application of force by an insertion tool.

22. The implantable transducer system of claim 20, wherein the outer surface of the implantable transducer and an inner surface of the at least one moveable member have corresponding screw threads so as permit distal movement of the at least one moveable member along the outer surface of the implantable transducer.

23. The implantable transducer system of claim 20, wherein the resiliently flexible member is a circumferential member substantially surrounding a section of an outer surface of the implantable transducer.

24. An implantable hearing prosthesis comprising the implantable transducer system of claim 15.

* * * * *